United States Patent [19]
Tehim et al.

[11] Patent Number: 6,103,715
[45] Date of Patent: Aug. 15, 2000

[54] DOPAMINE RECEPTOR LIGANDS

[75] Inventors: Ashok Tehim, Mississauga; Jian-Min Fu, Brampton; Sumanas Rakhit, Mississauga, all of Canada

[73] Assignee: Allelix Biopharmaceuticals Inc., Mississauga, Canada

[21] Appl. No.: 09/139,715

[22] Filed: Aug. 25, 1998

Related U.S. Application Data

[62] Division of application No. 08/642,264, May 3, 1996, Pat. No. 5,798,350, which is a division of application No. 08/355,297, Dec. 12, 1994, Pat. No. 5,538,965, which is a continuation-in-part of application No. 08/172,208, Dec. 23, 1993, abandoned.

[51] Int. Cl.$^7$ .................. A61K 31/55; C07D 243/10; C07D 487/12; C07D 491/00
[52] U.S. Cl. .................................... 514/220; 540/557
[58] Field of Search .............................. 540/557; 514/220

[56] References Cited

U.S. PATENT DOCUMENTS

| | | | |
|---|---|---|---|
| 3,539,573 | 11/1970 | Schmutz et al. | 260/268 |
| 3,546,226 | 12/1970 | Schmutz et al. | 260/268 |
| 3,751,415 | 8/1973 | Schmutz et al. | 260/268 |
| 3,758,479 | 9/1973 | Schmutz et al. | 260/268 |
| 3,884,922 | 5/1975 | Nakanishi et al. | 540/551 |
| 3,908,010 | 9/1975 | Schmutz et al. | 424/250 |
| 3,983,234 | 9/1976 | Sayers | 424/250 |
| 4,096,261 | 6/1978 | Horrum et al. | 424/250 |
| 5,354,747 | 10/1994 | Hansen, Jr. et al. | 514/211 |

FOREIGN PATENT DOCUMENTS

92/03138  3/1992  WIPO .

OTHER PUBLICATIONS

Coyne et al., "Antiinflammatory Dialkylaminoalkylureas", *J. Med. Chem.*, vol. 10:541–546, (1967).
Fitton et al., "Clozapine: A Review Of Its Pharmacological Properties, And The Therapeutic Use In Schizophrenia", *Drugs*, vol. 40:722–747, (1990).
Krogh et al., "Compendium of Pharmaceuticals and Specialties", *Canadian Pharmaceutical Association*, 28th ed., (1993).
Lahti et al., "Dompamine D$_4$ Versus D$_2$ Receptor Selectivity of Dopamine Receptor Antagonists: Possible Therapeutic Implications", *European Journal of Pharmacology*, vol. 236:483–486, (1993).
Seeman et al., "Dopamine D$_2$ Receptor Binding Sites For Agonists", *Molecular Pharmacology*, vol. 28:391–399, (1985).
Seeman et al., "Dopamine D$_4$ Receptors Bind Inactive (+)–aporphines, Suggesting Neuroleptic Role. Sulpiride Not Stereoselective", *European Journal of Pharmacology*, vol. 233:173–174, (1993).
Seeman et al., "Dopamine D4 Receptors Elevated in Schizophrenia", *Nature*, vol. 365:441–445, (1993).
Van Tol et al., "Cloning of The Gene For A Human Dopamine D$_4$ Receptor With High Affinity For the Antipsychotic Clozapine", *Nature*, vol. 350:610–614, (1991).
Van Tol et al., "Multiple Dopamine D$_4$ Receptor Variants In The Human Population", *Nature*, vol. 358:149–152, (1992).
Protiva et al., "Chemical Abstracts", vol. 90, No. 121655, (1978).
Jilek et al., "Chemical Abstracts", vol. 85, No. 46576, (1975).
Giani et al., "A New Facile Synthesis of 11–Oxo–10,11–dihydro–5H–dibenzol[$^{b,e}$][1$^,4$]diazepines", Synthesis, 1985, pp. 550–552.

(List continued on next page.)

*Primary Examiner*—Mukund J. Shah
*Assistant Examiner*—Bruck Kifle
*Attorney, Agent, or Firm*—Foley & Lardner

[57] ABSTRACT

Described herein are D4 receptor-selective compounds of the general formula:

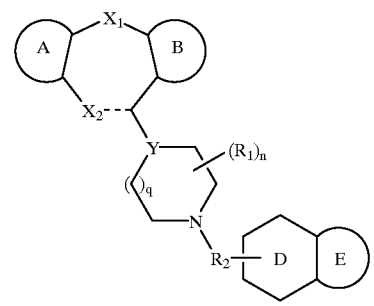

wherein:
  A and B are independently selected, optionally substituted, saturated or unsaturated 5- or 6-membered, homo- or heterocyclic rings;
  $X_1$ is selected from $CH_2$, O, NH, S, C=O, CH—OH, CH—N($C_{1-4}$alkyl)$_2$, C=CHCl, C=CHCN, N—$C_{1-4}$ alkyl, N-acetyl, $SO_2$ and SO;
  $X_2$ - - - is selected from N=, $CH_2$—, CH=, C(O)—, O—, and S—;
  $R_1$ represents $C_{1-4}$alkyl;
  Y is selected from CH and N;
  n is 0, 1 or 2;
  q is 1 or 2;
  $R_2$ is $C_{1-6}$alkyl optionally incorporating a heteroatom selected from N, O and S;
  D is cyclohexane or benzene; and
  E is a saturated or unsaturated 5- or 6-membered heterocycle incorporating 1, 2 or 3 heteroatoms selected from O, N, and S, wherein E is optionally substituted with 1 or 2 substituents selected from halogen, $C_{1-4}$alkyl and halogen-substituted $C_{1-4}$alkyl;

and acid addition salts, solvates and hydrates thereof. Their use as ligands for dopamine receptor identification and in a drug screening program, and as pharmaceuticals to treat indications in which the D4 receptor is implicated, such as schizophrenia, is also described.

20 Claims, No Drawings

OTHER PUBLICATIONS

Harris et al., "Affinity of 10–(4–Methylpiperazino)dibenz [$^b,^f$] oxepins for Clozapine and Spiroperidol Binding Sites in Rat Brain[1]", J. Med. Chem., 1982, 35, pp. 855–858.

Klunder et al., "Novel Non–Nucleoside Inhibitors of HIV–1 Reverse Transcriptase. 2. Tricyclic Pyridobenzoxazepinones and Dibenzoxazepinones", J. Med. Chem., 1992, 35, pp. 1887–1897.

de Paulis et al., "Synthesis of Clozapine Analogues and Their Affinity for Clozapine and Spiroperidol Binding Sites in Rat Brain[1]", J. Med. Chem., vol. 24, No. 9, Sep. 1981, pp. 1021–1026.

Holubek et al., "Noncataleptic Potential Neuroleptics: 2–Nitro and 2–Hydroxy Derivatives of 10–(4–zino)–10,11–Dihydrodibenzo[b,f]Thiepin*", Collec. Czech. Chem. Commun., Col. 42, 1977, pp. 2231–2239.

Sindler et al., "Noncataleptic Potential Neuroleptics: 2–Nitro and 2–Hydroxy Derivatives of 10–(4–Methylpiperazino)–10,11–Dihydrodibenzol[$^b,^f$]Thiepin*", Coll. Czech. Commun., 42, 1977, pp. 2231–2239.

DOPAMINE RECEPTOR LIGANDS

This application is a divisional of application Ser. No. 08/642,264, filed May 3, 1996 which is a divisional of a application Ser. No. 08/355,297, filed Dec. 12, 1994, now U.S. Pat. No. 5,538,965, which in turn is a continuation-in-part of application Ser. No. 08/172,208, filed Dec. 23, 1993.

This invention relates to compounds that bind to the dopamine D4 receptor, to their preparation and their use for therapeutic and drug screening purposes.

BACKGROUND TO THE INVENTION

Neuronal cell receptors that bind the neurotransmitter dopamine constitute a group of at least five structurally distinct proteins that can now be produced using recombinant DNA techniques. These techniques have been applied to construct cell lines that incorporate the dopamine receptor in their membranes, to provide regenerable and homogeneous substrates with which chemical libraries can be screened to identify potential CNS-active drugs.

Recent evidence strongly implicates the dopamine receptor classified as D4 in the etiology of schizophrenia. It has been suggested that compounds capable of interfering with the function of this receptor, which is present in schizophrenics at levels that are six times normal, would be useful in the treatment of this disease (Seeman et al, Nature, 1993, 365:441). Some drugs currently on the market in fact exhibit the desired antagonism of D4 receptor activity, and bind with relative strong affinity to the receptor. Yet because of their structure, these drugs interact also with related dopamine receptors, particularly the D2 receptor type, which results in significant side effects that include altered motor function and tachycardia. It would be desirable to provide compounds that exhibit not only a high degree of affinity for the D4 receptor, but also a relatively low degree of affinity for the D2 receptor. In this specification, this desired combination of receptor binding properties is referred to as D4 selectivity.

Products currently marketed to treat indications in which the D4 receptor function is implicated include the dibenzodiazepine, clozapine, and the dibenzoxazepine, isoloxapine. Analysis of their dopamine receptor binding properties has shown that the preference for binding the D4 receptor relative to the D2 receptor is about 10 fold, for both products. Similarly, both bind the D4 receptor with about the same affinity (Ki value approximately 20 nM). Other products, recently published in the scientific literature, have shown similar D4 to D2 selectivity profile and D4 affinity values.

It is an object of the present invention to provide a compound having an improved D4 selectivity profile.

It is another object of the present invention to provide a compound having an improved D4 binding affinity.

It is another object of the present invention to provide a compound having both an improved D4 selectivity profile and D4 binding affinity.

It is a further object of the present invention to provide a pharmaceutical composition comprising a compound of the present invention, as active ingredient.

SUMMARY OF THE INVENTION

According to one aspect of the present invention, there is provide a compound of Formula I:

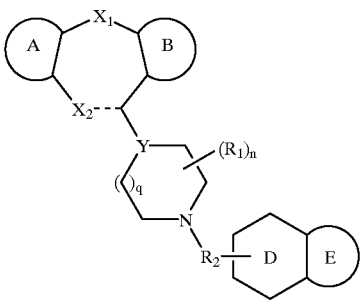

wherein:

A and B are independently selected, optionally substituted, saturated or unsaturated 5- or 6-membered, homo- or heterocyclic rings;

$X_1$ is selected from $CH_2$, O, NH, S, C=O, CH—OH, CH—N($C_{1-4}$alkyl)$_2$, C=CHCl, C=CHCN, N—$C_{1-4}$ alkyl, N-acetyl, $SO_2$ and SO;

$X_2$ - - - is selected from N=, $CH_2$—, CH=, C(O)—, O—, and S—;

Y is selected from CH and N;

$R_1$ represents $C_{1-4}$alkyl;

n is 0, 1 or 2;

q is 1 or 2;

$R_2$ is $C_{1-6}$alkyl optionally incorporating a heteroatom selected from N, O and S;

D is cyclohexane or benzene; and

E is a saturated or unsaturated 5- or 6-membered heterocycle incorporating 1, 2 or 3 heteroatoms selected from O, N, and S, wherein E is optionally substituted with 1 or 2 substituents selected from halogen, $C_{1-4}$alkyl and halogen-substituted $C_{1-4}$alkyl;

and acid addition salts, solvates and hydrates thereof.

According to another aspect of the invention, there is provided a pharmaceutical composition comprising a compound of Formula I and a pharmaceutically acceptable carrier.

In a further aspect of the invention, there is provided an analytical method in which a compound of the invention is used either to distinguish the D4 receptor from other receptor types or from the D2 receptor.

These and other aspects of the present invention are now described in greater detail hereinbelow.

DETAILED DESCRIPTION AND PREFERRED EMBODIMENTS

The invention relates to compounds that bind the dopamine D4 receptor in a selective manner, relative to the dopamine D2 receptor. It has been found, more particularly, that the D4 selectivity of D4-binding ligands having the tricyclic structure:

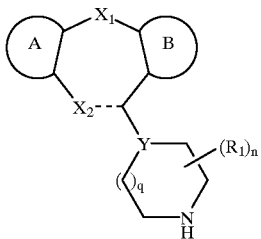

is significantly improved when the piperazine group is derivatized by a function having the structure:

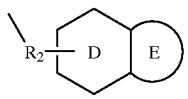

In accordance with one of its aspects, the present invention accordingly provides compounds that conform to Formula I:

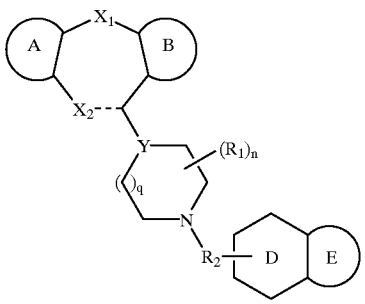

In embodiments of the invention, the rings D and E together form an optionally bicyclic structure, in which ring D is benzene and ring E is a 5- or 6-membered heterocycle that comprises 2 or 3 heteroatoms selected from O, N and S. Ring E is optionally substituted with 1 or 2 substituents selected from halogen such as Cl or F; $C_{1-4}$alkyl such as methyl; and halogen-substituted $C_{1-4}$alkyl such as trifluoromethyl. Particular embodiments of the invention include those in which ring D is benzene and ring E is a saturated, 5-membered ring containing two heteroatoms, such as 1,3-dioxolane, thiazole, imidazole, 2-imidazoline, imidazolidine, and 1,2,3-triazole. In a specific embodiment of the invention, rings D and E together form 1,3-benzodioxolane.

The $R_2$ function coupled between ring D and the piperazinyl group is, in embodiments of the invention, a linear or branched chain $C_{1-6}$alkylene group such as —$CH_2$—, —$CH(CH_3)$—, —$C(CH_3)_2$— and —$CH_2$—$CH_2$—. The $C_{1-6}$alkylene group may be interrupted or terminated by a heteroatom such as oxygen or sulfur, to form a group such as —O—$CH_2$—, —$CH_2$—O—$CH_2$—, —$CH_2$—O—. The $R_2$ group can be coupled to ring D at the meta/para position.

In a specifically preferred embodiment of the invention, the function represented in Formula I by the symbols —$R_2$—D/E is the piperonyl group.

The tricyclic function to which the $R_2$—D/E function is coupled can have various structures and will typically incorporate those found to be important for dopamine D4 receptor binding. In other words, the tricycles suitable for coupling to the $R_2$—D/E function are those which, when substituted by functions other than $R_2$—D/E, are determined by the assay herein described to bind the D4 receptor (preferably the human D4 receptor) with an affinity not greater than 1 $\mu$M (Ki). In particular, the rings A and B are selected, according to embodiments of the invention, from benzene, pyridine, pyrimidine, pyrazine, pyridazine, pyrole, imidazole, triazole, pyrazole, thiophene, thiazole, and pyran. In a particular embodiment, ring A is selected from benzene and pyridine and ring B is selected from benzene, pyridine, pyrimidine, pyrazine, pyridazine, pyrole, imidazole, triazole, pyrazole, thiophene, thiazole, furan and pyran; and is particularly selected from benzene and pyridine. In specific embodiments of the invention, both ring A and B are benzene. It is to be appreciated that when rings A and B are heterocycles, the heteroatorris are shared with the central seven membered ring only when the shared heteroatom is N. Such tricycles are within the scope of the Formula I; one embodiment of which is described by Lednicer et al in *The Organic Chemistry of Drug Synthesis*, (1992, John Wiley & Sons Inc., New York) wherein ring B is imidazole that is fused to a thiazepine at one of the imidazole nitrogen atoms.

One or both rings A and B may be substituted with from 1 to 3, usually 1 or 2, substituents. When substituted, the substituents are selected from hydroxyl, halo, $C_{1-4}$alkyl, amino, nitro, cyano, halo-substituted $C_{1-4}$alkyl, $C_{1-4}$alkoxy, halo-substituted $C_{1-4}$alkoxy, $C_{1-4}$alkoxycarbonyl, $C_{1-4}$acyl, halo-substituted $C_{1-4}$acyl, cyclo-$C_{3-7}$alkyl, thio-$C_{1-4}$alkylene, $C_{1-4}$alkylthio, halo-substituted $C_{1-4}$alkylthio, cyanothio, tetrazolyl, N-piperidinyl, N-piperazinyl, N-morpholinyl, acetamido, $C_{1-4}$alkylsulfonyl, halosulfonyl, halo-substituted $C_{1-4}$alkylsulfonyl, $C_{1-4}$alkylsulfoxyl, sulfonamnido, $C_{1-4}$alkylseleno, and $OSO_3H$.

Substitution sites on rings A and B will be limited in practice to the carbon atoms on the ring that are not shared with the central seven membered ring. For example, a benzene ring can accomodate up to 4 substituents; pyridline, and pyran rings can accomodate up to 3 substituents; pyrimidine, pyrazine, pyridazine, pyrole, furan and thiophene rings can accomodate up to 2 substituents; imidazole, pyrazole and thiazole rings can accomodate only 1 substituent; and a triazole ring can accomodate no substituents. It is also to be understood that rings A and B may incorporate substituents at nitrogen atoms on the ring that are not shared with the central seven membered ring. For example the NH member of an imidazole ring may be substituted.

In particular embodiments, rings A and B are substituted with from 1 to 2 substituents selected from chloro, fluoro, methyl, trifluoromethyl, methoxy, nitro, cyano and methylthio. In particularly preferred embodiments ring A is benzene substituted with 1 or 2 substituents selected from chloro, methyl, nitro and cyano and ring B is benzene substituted with 1 or 2 substituents selected from chloro, methoxy, trifluoromethyl and nitro.

In the central, 7-membered ring of the tricycle, $X_1$ may be any one of $CH_2$, O, NH, S, C=O, CH—OH, CH—N($C_{1-4}$alkyl)$_2$, C=CHCl, C=CHCN, N—$C_{1-4}$alkyl, N-acetyl, $SO_2$ and SO, while $X_2$ - - - may be any one of N=, $CH_2$—, CH=, C(O)—, O—, and S—. In a particular embodiment of the invention, $X_1$ is O, S or NH. In another embodiment, $X_2$ - - - is N= or CH=. In a particularly preferred embodiment, $X_1$ is O, S or NH and $X_2$ - - - is N= or CH=. In specific embodiments $X_1$ and $X_2$ - - - are selected to form a seven membered ring selected from oxazepine, diazepine, thiazepine and thiepine.

In preferred embodiments $X_1$ and $X_2$ - - - together with rings A and B are selected to form a tricycle that is selected from 5H-dibenzo[b,e][1,4]diazepine that is optionally substituted, for example with one of 7,8-dichloro, 7,8-dimethyl, 2-chloro, 3-chloro, 4-chloro, 2,4-dichloro, 4,7,8-trichloro, 2-trifluoromethyl, 1-fluoro, or 2-methoxy; dibenz[b,f][1,4]oxazepine that is optionally substituted, for example with one of 4-nitro, 8-chloro, 4-cyano or 4-chloro; dibenzo[b,f]thiepine that is optionally substituted, for example with one of 2-nitro or 2-chloro; 11H-dibenzo[b,f]thiepine that is optionally substituted, for example with 2-methylthio; and dibenzo[b,f][1,4]thiazepine that is optionally substituted, for example with 8-chloro. In a specific embodiment of the invention, $X_1$ and $X_2$ - - - together with rings A and B are selected to form a tricycle that is selected from:

dibenz[b,f][1,4]oxazepine;
8-chlorodibenz[b,f][1,4]oxazepine;
8-methyidibenz[b,f][1,4]oxazepine;
7,8-dimethyl-5H-dibenzo[b,e][1,4]diazepine;
5H-dibenzo[b,e][1,4]diazepine;
2-chloro-5H-dibenzo[b,e][1,4]diazepine;
8-chlorodibenzo[b,f][1,4]thiazepine;
4-chloro-5H-dibenzo[b,e][1,4]diazepine;
7,8-dichloro-5H-dibenzo[b,e][1,4]diazepine;
2-trifluoromethyl-5H-dibenzo[b,e][1,4]diazepine;
2,7,8-trichloro-5H-dibenzo[b,e][1,4diazepine;
3-chloro-5H-dibenzo[b,e][1,4]diazepine;
2-methoxy-5H-dibenzo[b,e][1,4]diazepine;
4-cyanodibenz[b,f][1,4]oxazepine;
4-chlorodibenz[b,f][1,4]oxazepine;
4-nitrodibenz[b,f][1,4]oxazepine; and
2-nitrodibenzo[b,f]thiepine.

In a particular embodiment, $X_1$ and $X_2$ - - - together with rings A and B are selected to form a tricycle that is selected from:

dibenz[b,f][1,4]oxazepine;
8-chlorodibenz[b,f][1,4]oxazepine;
8-methyidibenz[b,f][1,4]oxazepine;
7,8-dimethyl-5H-dibenzo[b,e][1,4]diazepine;
5H-dibenzo[b,e][1,4]diazepine;
8-chlorodibenzo[b,f][1,4]thiazepine;
2-methoxy-5H-dibenzo[b,e][1,4]diazepine;
7,8-dichloro-5H-dibenzo[b,e][1,4diazepine;
2-trifluoromethyl-5H-dibenzo[b,e][1,4]diazepine;
2,7,8-trichloro-5H-dibenzo[b,e][1,4]diazepine; and
2-nitrodibenzo[b,f]thiepine.

In a preferred embodiment, $X_1$ and $X_2$ - - - together with rings A and B are selected to form a tricycle that is selected from:

dibenz[b,f][1,4]oxazepine;
8-chlorodibenz[b,f][1,4]oxazepine;
8-methyldibenz[b,f][1,4]oxazepine;
7,8-dimethyl-5H-dibenzo[b,e][1,4diazepine;
5H-dibenzo[b,e][1,4]diazepine;
8-chlorodibenzo[b,f][1,4]thiazepine; and
2-methoxy-5H-dibenzo[b,e][1,4]diazepine.

In another preferred embodiment, $X_1$ and $X_2$ - - - together with rings A and B are selected to form a tricycle that is selected from:

dibenz[b,f][1,4]oxazepine;
8-chlorodibenz[b,f][1,4]oxazepine;
7,8-dimethyl-5H-dibenzo[b,e][1,4]diazepine;
8-chlorodibenzo[b,f][1,4]thiazepine;
4-chloro-5H-dibenzo[b,e][1,4]diazepine;
7,8-dichloro-5H-dibenzo[b,e][1,4]diazepine;
2,7,8-trichloro-5H-dibenzo[b,e][1,4]diazepine;
3-chloro-5H-dibenzo[b,e][1,4]diazepine;
4-nitrodibenz[b,f][1,4]oxazepine;
2-nitrodibenzo[b,f]thiepine; and
2-chlorodibenzo[b,f]thiepine.

In another preferred embodiment, $X_1$ and $X_2$ - - - together with rings A and B are selected to form a tricycle that is selected from:

8-chloro-11-(4-piperonyl)-1-piperazinyl)-dibenz[b,f][1,4]oxazepine;
2-methoxy-11-(4-piperonyl-1-piperazinyl)-5H-dibenzo[b,e][1,4]diazepine; and
2-nitro-10-(4-piperonyl-1-piperazinyl)dibenzo[b,f]thiepine.

In a more preferred embodiment, $X_1$ and $X_2$ - - - together with rings A and B are selected to form a tricycle that is selected from:

2-nitrodibenzo[b,f]thiepine; and
8-chlorodibenz[b,f][1,4]oxazepine.

In a most preferred embodiment, $X_1$ and $X_2$ - - - together with rings A and B form a tricycle that is 8-chlorodibenz[b,f][1,4]oxazepine.

In an embodiment of the invention, the ring coupled to the tricyclic structure may incorporate 0, 1 or 2 $R_1$ substituents that are $C_{1-4}$alkyl groups, such as methyl. The piperazinyl ring may incorporate an additional $CH_2$ group (q=2) to form a diazepine ring as described by Horrom et al (U.S. Pat. No. 4,096,261). In another embodiment of the invention, Y is N or CH thereby forming a piperazinyl or piperidinyl ring respectively.

In particular embodiments of the invention, n is 0; q is 1 and Y is N. In a specific embodiment n, q and Y are chosen to give an unsubstituted piperazinyl ring.

Specific compounds of formula (I) include:
11-(4-piperonyl)-1-piperazinyl)-dibenz[b,f][1,4]oxazepine;
8-chloro-11-(4-piperonyl)-1-piperazinyl)-dibenz[b,f][1,4]oxazopine;
8-methyl-11-(4-piperonyl)-1-piperazinyl)-dibenz[b,f][1,4]oxazepine;
7,8-dimethyl-11-(4-piperonyl-1-piperazinyl)-5H-dibenzo[b,e][1,4]diazepine;
11-(4-piperonyl-1-piperazinyl)-5H-dibenzo[b,e][1,4]diazepine;
2-chloro-11-(4-piperonyl-1-piperazinyl)-5H-dibenzo[b,e][1,4]diazepine;
8-chloro-11-(4-piperonyl-1-piperazinyl)dibenzo[b,f][1,4]thiazepine;
4-chloro-11-(4-piperonyl-1-piperazinyl)-5H-dibenzo[b,e][1,4]diazepine;
7,8-dichloro-11-(4-piperonyl-1-piperazinyl)-5H-dibenzo[b,e][1,4]diazepine;
2-trifluoromethyl-11-(4-piperonyl-1-piperazinyl)-5H-dibenzo[b,e][1,4]diazepine;
2,7,8-trichloro-11-(4-piperonyl-1-piperazinyl)-5H-dib-enzo[b,e][1,4]diazepine;
3-chloro-11-(4-piperonyl-1-piperazinyl)-5H-dibenzo[b,e][1,4]diazepine;
2-methoxy-11-(4-piperonyl-1-piperazinyl)-5-dibenzo[b,e][1,4]diazepine;
4-cyano-11-(4-piperonyl-1-piperazinyl)dibenz[b,f][1,4]oxazepine;
4-chloro-11-(4-piperonyl-1-piperazinyl)dibenz[b,f][1,4]oxazepine;
4-nitro-11-(4-piperonyl)-1-piperazinyl)-dibenz[b,f][1,4]oxazepine; and
2-nitro-10-(4-piperonyl-1-piperazinyl)dibenzo[b,f]thiepine.

In a particular embodiment, there are provided compounds of formula (1) exhibiting better D4selectivity than the corresponding 4-methyl piperazine compound, including:
11-(4-piperonyl)-1-piperazinyl)-dibenz[b,f][1,4]oxazepine;

8-chloro-11-(4-piperonyl)-1-piperazinyl)-dibenz[b,f][1,4] oxazepine;
8-methyl-11-(4-piperonyl)-1-piperazinyl)-dibenz[b,f][1,4] oxazepine;
7,8-dimethyl-11-(4-piperonyl-1-piperazinyl)-5H-dibenzo[b,e][1,4]diazepine;
11-(4-piperonyl-1-piperazinyl)-5H-dibenzo[b,e][1,4] diazepine;
8-chloro-11-(4-piperonyl-1-piperazinyl)dibenzo[b,f][1,4] thiazepine;
2-methoxy-11-(4-piperonyl-1-piperazinyl)-5H-dibenzo[b,e][1,4]diazepine;
7,8-dichloro-11-(4-piperonyl-1-piperazinyl)-5H-dibenzo[b,e][1,4]diazepine;
2-trifluoromethyl-11-(4-piperonyl-1-piperazinyl)-5H-dibenzo[b,e][1,4]diazepine;
2,7,8-trichloro-11-(4-piperonyl-l1-piperazinyl)-5H-dibenzo[b,e][1,4]diazepine; and
2-nitro-10-(4-piperonyl-1-piperazinyl)dibenzo[b,f]thiepine.

In a more preferred embodiment, there are provided compounds of formula (I) exhibiting better D4 affinity and selectivity than the corresponding 4-methyl piperazine compound, including:
11-(4-piperonyl)-1-piperazinyl)-dibenz[b,f][1,4]oxazepine;
8-chloro-11-(4-piperonyl)-1-piperazinyl)-dibenz[b,f][1,4] oxazepine;
8-methyl-11-(4-piperonyl)-1-piperazinyl)-dibenz[b,f][1,4] oxazepine;
7,8-dimethyl-11-(4-piperonyl-1-piperazinyl)-5H-dibenzo[b,e][1,4]diazepine;
11-(4-piperonyl-1-piperazinyl)-5H-dibenzo[b,e][1,4] diazepine;
8-chloro-11-(4-piperonyl-1-piperazinyl)dibenzo[b,f][1,4] thiazepine; and
2-methoxy-11-(4-piperonyl-1-piperazinyl)-5H-dibenzo[b,e][1,4]diazepine.

In a more preferred embodiment, there are provided compounds of formula (I) exhibiting better D4 selectivity than clozapine, including:
11-(4-piperonyl)-1-piperazinyl)-dibenz[b,f][1,4]oxazepine;
8-chloro-11-(4-piperonyl)-1-piperazinyl)-dibenz[b,f][1,4] oxazepine;
7,8-dimethyl-11-(4-piperonyl-1-piperazinyl)-5H-dibenzo[b,e][1,4]diazepine;
8-chloro-11-(4-piperonyl-1-piperazinyl)dibenzo[b,f][1,4] thiazepine;
4-chloro-11-(4-piperonyl-1-piperazinyl)-5H-dibenzo[b,e][1,4]diazepine;
7,8-dichloro-11-(4-piperonyl-1-piperazinyl)-5H-dibenzo[b,e][1,4]diazepine;
2,7,8-trichloro-11-(4-piperonyl-1-piperazinyl)-5H-dibenzo[b,e][1,4]diazepine;
3-chloro-11-(4-piperonyl-1-piperazinyl)-5H-dibenzo[b,e][1,4]diazepine;
4-nitro-11-(4-piperonyl)-1-piperazinyl)-dibenz[b,f][1,4] oxazepine;
4-cyano-11-(4-piperonyl-1-piperazinyl)dibenz[b,f][1,4] oxazepine;
4-chloro-11-(4-piperonyl-1-piperazinyl)dibenz[b,f][1,4] oxazepine;
2-nitro-10-(4-piperonyl-1-piperazinyl)dibenzo[b,f]thiepine; and
2-chloro-10-(4-piperonyl-1-piperazinyl)dibenzo[b,f] thiepine.

In a more preferred embodiment, there are provided compounds of formula (I) exhibiting better D4 affinity than clozapine, including:
8-chloro-11-(4-piperonyl)-1-piperazinyl)-dibenz[b,f][1,4] oxazepine;
2-methoxy-11-(4-piperonyl-1-piperazinyl)-5H-dibenzo[b,e][1,4]diazepine; and
2-nitro-10-(4-piperonyl-1-piperazinyl)dibenzo[b,f]thiepine.

In a more preferred embodiment, there are provided compounds of formula (I) exhibiting better D4 affinity and selectivity than clozapine, including:
2-nitro-10-(4-piperonyl-1-piperazinyl)dibenzo[b,f]thiepine; and
8-chloro-11-(4-piperonyl)-1-piperazinyl)-dibenzo[b,f][1,4] oxazepine.

In a most preferred embodiment, there are provided compounds of formula (I) that exhibit D4 affinity and selectivity that is better than clozapine and the corresponding 4-methyl compound, such a compound is 8-chloro-11-(4-piperonyl)-1-piperazinyl)-dibenz[b,f][1,4]oxazepine.

Acid addition salts of the compound of Formula I include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of Formula I for ligand use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

It will be appreciated that certain compounds of Formula I may contain an asymmetric centre. Such compounds will exist as two (or more) optical isomers (enantiomers). Both the pure enantiomers and the racemic mixtures (50% of each enantiomer), as well as unequal mixtures of the two, are included within the scope of the present invention. Further, all diastereomeric forms possible (pure enantiomers and mixtures thereof) are within the scope of the invention.

The compounds of the present invention can be prepared by processes analogous to those known in the art. The present invention therefore provides, in a further aspect, a process for the preparation of a compound of Formula I or a salt, solvate or hydrate thereof, which comprises the step of coupling a reagent of Formula A:

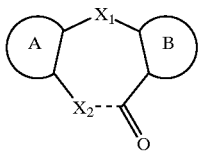

with a reagent of Formula B:

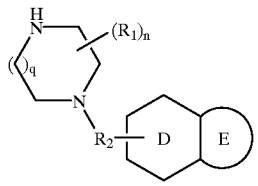

using a Lewis acid such as $TiCl_4$ or $BF_3 \cdot Et_2O$.

Reagent (A) can be obtained commercially or can be synthesized using established ring closure procedures. For example, when $X_1$ is NH and $X_2$ - - - is N= (a diazepine), reagent (A) may be prepared according to the procedures described by Giani et al (Synthesis, 1985, 550) by refluxing equimolar amounts of 2-chlorobenzoic acid, o-phenylenediamine and powdered copper in chlorobenzene. The following is a schematic representation of the reaction to obtain the diazepine form of reagent (A):

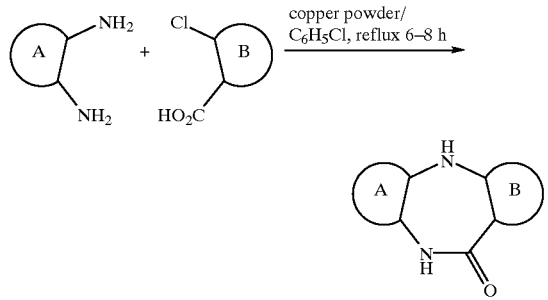

When $X_1$ is O and $X_2$ - - - is N= (an oxazepine), reagent (A) may be prepared according to the procedures described by Klunder (J. Med. Chem. 1992, 35:1887) by condensation of a 2-aminophenol with 2-chloro-5-nitrobenzoyl chloride in THF to afford the corresponding carboxamide followed by refluxing with NaOH for ring closure. The following is a schematic representation of the steps to obtain the is oxazepine form of reagent (A):

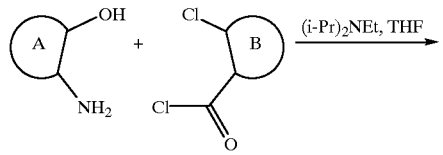

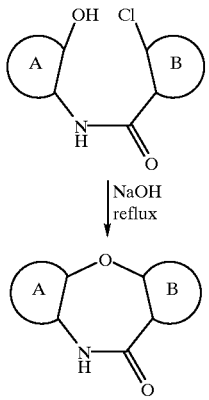

The thiepine form of reagent (A), i.e. when $X_1$ is S and $X_2$ - - - is CH=, may be prepared according to the procedures described by Sindelar et al (Collect. Czech. Chem. Commun, 1983, 48(4):1187). When reagent (A) is an oxepine i.e. when $X_1$ is O and $X_2$ - - - is $CH_2$—, it may be prepared in the manner reported by Harris et al (J. Med. Chem., 1982, 25(7):855); and the corresponding cycloheptene reagent (A) i.e. when $X_1$ and $X_2$ - - - are both $CH_2$, may be prepared as reported by De Paulis et al (J. Med. Chem. 1981, 24(9):1021). The thiazepine reagent (A) may be prepared in a four step process starting from 1-bromo-2-nitrobenzene and methyl thiosalicylate. The steps involve coupling; reduction of the nitro group; hydrolysis of the ester group; and finally ring closure.

Many of the reagents of Formula B are similarly available from various commercial sources. In the alterative, or where the desired reagent B is not commercially available, it can be synthesized from the corresponding 1-piperazinecarboxaldehyde by reaction with Halo-$R_2$—D/E, where halo is desirably the bromo derivative. Regnier et al (U.S. Pat. No. 3,119,826) describes the synthesis of piperonyl substituted piperazine by reacting piperazine with piperonyl chloride which is first prepared by chlorinating the corresponding alcohol with $SOCl_2$. The alcohol may be prepared by reducing the corresponding carboxy-substituted compound with a suitable reducing agent such as borane-THF complex or borane-$Me_2S$ complex. The carboxyl compound may incorporate various heteroatoms in ring E which are commercially available, for example benzothiazole-6-carboxylic acid (,Maybridge 04-7305), 5-benzimidazolecarboxylic acid (Aldrich 29,678-3) and benzotriazole-5-carboxylic acid (Aldrich 30,423-9).

In the specific case where Y=CH, synthesis proceeds by coupling isonicotinic acid (4-piperonyl derivative thereof) with an amino reagent of the formula:

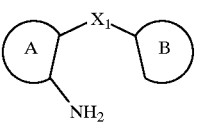

using a suitable coupling agent such as EDCl, to form an amide intermediate. The amino reagent may be obtained commercially or may be synthesized according to established synthetic techniques. For example, 2-chloronitrobenzene can be converted to the amino reagent 2-aminodiphenylsulphide (or oxide) by substitution with thiobenzene (or hydroxybenzene) in the presence of $K_2CO_3$ and then reducing in the presence of Zn. The resulting amide intermediate can then be cyclized with a suitable ring closure agent such as POCl₃ to give the final compound according to formula I wherein Y is CH.

For use as a ligand, the present compounds can be stored in packaged form for reconstitution and use. The compounds can be used to distinguish dopamine receptors from other receptor types, for example glutamate and opioid receptors, within a population of receptors and in particular to distinguish between the D4 and D2 receptors. The latter can be achieved by incubating preparations of the D4 receptor and of the D2 receptor with a D4 selective compound of the invention and then incubating the resulting preparation with a radiolabelled dopamine receptor ligand, such as $^3$H-spiperone. The D2 and D4 receptors are then distinguished by determining the difference in membrane-bound radioactivity, with the D4 receptor exhibiting lesser radioactivity, i.e., lesser $^3$H-spiperone binding.

In another embodiment of the invention, the compound is provided in labelled form, such as radiolabelled form e.g. labelled by incorporation within its structure of $^3$H or $^{14}$C or by conjugation to $^{125}$I. Such radiolabelled forms can be used to directly to distinguish between dopamine D4 and dopamine D2 receptors. Furthermore, radiolabelled forms of the present compounds can be exploited to screen for more potent dopamine D4 ligands, by determining the ability of the test ligand to displace the radiolabelled compound of the present invention.

The clozapine-like binding profile of the present compounds indicates their utility as pharmaceuticals that may be useful for the treatment of various conditions in which the use of a dopamine D4 receptor ligand is indicated, such as for the treatment of anxiety and schizophrenia.

For use in medicine, the compounds of the present invention are usually administered in a standard pharmaceutical composition. The present invention therefore provides, in a further aspect, pharmaceutical compositions comprising an effective amount of a compound of Formula I or a pharmaceutically acceptable salt, solvate or hydrate thereof and a pharmaceutically acceptable carrier.

The compounds of the present invention may be administered by an convenient route, for example by oral, parenteral, buccal, sublingual, nasal, rectal or transdermal administration and the pharmaceutical compositions forrriulated accordingly.

The compounds and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into hard gelatin capsule; alternatively, a dispersion or suspension can be prepared using any suitable pharmaceutical carrier, for example aqueous gums, celluliscs, silicates or oils and the dispersion or suspension filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non- aqueous solvent and are usually presented in single or mulitidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as flurochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine.

Compositions for rectal administration are conveniently in the form of suppositories containing a conventional suppository base such as cocoa butter.

Preferably, the composition is in unit dose form such as a tablet, capsule or ampoule. Suitable unit doses i.e. therapeutically effective amounts; can be determined during clinical trials designed appropriately for each of the condition for which administration of a chosen compound is indicated and will of course vary depending on the desired clinical endpoint. It is anticipated that dosage sizes appropriate for administering the compounds of the examples will be roughly equivalent to, or slightly less than, those used currently for clozapine. Accordingly, each dosage unit for oral administration may contain from 1 to about 500 mgs, and will be administered in a frequency appropriate for initial and maintenance treatments.

EXAMPLE 1

11-(4-piperonyl)-1-piperazinyl)-dibenz[b,f][1,4oxazepine

To a stirred solution of dibenz[b,f][1,4]oxazepin-11 (10H)-one (0.500 g, 2.37 mmol; Aldrich) in dry toluene (20.0 mL) at room temperature was added 1-piperonylpiperazine (2.40 g, 10.89 mmol; Aldrich) followed by the dropwise addition of TiCl₄ (1M in toluene, 2.85 mL, 2.85 mmol). The reaction mixture was refluxed for 2 hours, cooled to room temperature and then poured into an ammonium hydroxide solution (30%, 50 mL). The resulting mixture was extracted with dichloromethane (4×75 mL), and the combined organic phases were then dried (K₂CO₃) and concentrated. Purification of the product was conducted on silica gel using ethyl acetate:hexane (50:50) as the eluant to give 0.971 g (99%) of the title compound as a pale yellow solid; m.p. 128–130° C.

The hydrochloride salt of the title compound was subsequently prepared by dissolving the base (0.100 g , 0.242 mmol) in 1 mL of 3N-HCl in ethyl acetate, then stirring at room temperature for 15 minutes. The solution was removed under vacuum and the resulting oil was triturated with dry methanol (5.00 mL). The solvent was evaporated under reduced pressure to yield 0.111 g (quantitative) of the hydrochloride salt, as a colourless solid; m.p. 188–190° C. (decomp.).

In a like manner, there is prepared the following additional compound:
11-(4-piperonyl)-1-piperazinyl)-dibenzo[b,f][1,4] thiazepine,
from 10,11-dihydrodibenzo[b,f][1,4]thiazepin-11-one.

EXAMPLE 2

8-chloro-11-(4-piperonyl)-1-piperazinyl)dibenz[b,f][1,4]oxazepine

The title compound was produced in the manner described in example 1, but using the 8-chloro analog of dibenz[b,f][1,4]oxazepin-11(10H)-one as starting material, for reaction with 1-piperonylpiperazine. The 8-chloro compound was produced according to the protocol reported by Coyne and Cusic in J. Med. Chem., 1967, 10:541. Briefly, this entailed coupling potassium salicylaldehyde with :2,5-dichloronitrobenzene, followed by oxidation to the carboxylic acid, reduction of nitro, and finally ring closure, to yield the desired 8-chloro starting material (m.p.=256–258° C.).

The 8-chloro starting material was then reacted with 1-piperonylpiperazine in the manner described in example 1, and the title compound was obtained as a colourless solid; m.p.=62–64° C.

The hydrochloride salt of the title compound was subsequently prepared by dissolving the base (0.030 g, 0.067 mmol) in 0.3 mL of 3N-HCl in ethyl acetate, then stirring at room temperature for 15 minutes. The solution was removed under vacuum and the resulting oil was triturated with dry methanol (2.00 mL). The solvent was evaporated under reduced pressure to yield 0.033 g (quantitative) of the hydrochloride salt, as a colourless solid; m.p.=176–178° C.

In a like manner, there is prepared the following additional compound:
8-chloro-11-(4-piperonyl)-1-piperazinyl)-5H-dibenzo[b,e][1,4]diazepine; from
8-chloro-10,11-dihydro-5H-dibenzo[b,e][1,4]diazepin-11-one; and

EXAMPLE 3

8-methyl-11-(4-piperonyl)-1-piperazinyl)dibenz[b,f][1,4]oxazepine

The title compound was produced in the manner described in example 1, but using the 8-methyl analog of dibenz[b,f][1,4]oxazepin-11(10H)-one as starting material, for reaction with 1-piperonylpiperazine. The 8-methyl compound was produced according to the protocol reported by Klunder et al. in J. Med. Chem., 1992, 35:1887. Briefly, this entailed coupling 2-bromobenzoic acid with 2-amino-4-methylphenol, followed by cyclization using potassium hydroxide in dimethylformamide to yield the desired 8-methyl starting material (m.p. 207–208° C).

The 8-methyl starting material was then reacted with 1-piperonylpiperazine in the manner described in example 1, and the title compound was obtained (after recrystallization from 10% methylene chloride in hexanes)as white crystals; 50% yield; Rf (30% acetone/hexane) 0.4; m.p. 146–147° C.; HRMS (FAB): MH$^+$ for $C_{26}H_{25}N_3O_3$ calculated 428.1974, found 428.1939.

EXAMPLE 4

7,8-dimethyl-11-(4-piperonyl)-1-piperazinyl)-5H-dibenzo[b,f][1,4]diazepine

The title compound was produced in the manner described in example 1, but using the 7,8-dimethyl analog of 10,11-dihydro-5H-dibenzo[b,f][1,4]diazepin-11-one as starting material, for reaction with 1-piperonylpiperazine. The 7,8-dimethyl compound was prepared according to the procedure described by Giani et al. Synthesis, 1985, 550.

The 7,8-dimethyl starting material was then reacted with 1-piperonylpiperazine in the manner described in example 1, and the title compound was obtained as a yellow solid; 42% yield; Rf (50% acetone/hexane) 0.6; m.p. 176–178° C.; HRMS (FAB): MH$^+$ for $C_{27}H_{29}N_4O_2$ calculated 441.2291 found 441.2302.

EXAMPLE 5

11-(4-piperonyl)-1-piperazinyl-5H-dibenzo[b,e][1,4]diazepine

The desired starting material 10,11-dihydro-5H-dibenzo[b,e]1,4]diazepin-11-one was produced according to the protocol reported by Giani et. al. (supra). The tricyclic lactam was then reacted with 1-piperonylpiperazine in the manner described in example 1, and the title compound was obtained as a yellow solid (50%); m.p. 136–38° C.

EXAMPLE 6

2-Chloro-11-(4-piperonyl)-1-piperazinyl-5H-dibenzo[b,e][1,4]diazepine

The desired starting material 2-chloro-10,11-dihydro-5H-dibenzo[b,e][1,4]diazepin-11-one was produced according to the protocol reported by Giani et.al. (supra). The 2-chloro lactam was then reacted with 1-piperonylpiperazine in the manner described in example 1, and the title compound was obtained as a yellow-orange solid (92%); m.p. 60–64° C.

EXAMPLE 7

8-chloro-11-(4-piperonyl)-1-piperazinyl)dibenzo[b,f][1,4]thiazepine

The desired starting material 8-chloro-10,11-dihydrodibenzo[b,f][1,4]thiazepine-11-one was prepared in four steps starting from 2,5-dichloronitrobenzene and methyl thiosalicylate. The steps involved were coupling; reduction of nitro group; hydrolysis of ester group; and ring closure.

A solution of NaH (1.1 g, 40 mmol) in dry THF (20 mL) was cooled to 0° C. To this mixture methyl thiosalicylate (5.1 mL, 36 mmol) was added dropwise via syringe. The reaction mixture was warmed to room temperature to ensure completion of the reaction. The solution was cooled to 0° C. and 2,5-dichloronitrobenzene (7.0 g, 36 mmol) was added dropwise in THF (20 mL). The reaction was stirred at 0° C. for 30 minutes then stirred at room temperature for 4 h. The reaction was quenched with 5 mL ice cold water and then diluted with EtOAc (300 mL). The phases were separated and the organic phase was washed with sat. NaHCO$_3$, water and brine. The organic phase was dried (MgSO$_4$) and concentrated in vacuo. Recrystallization was done in CHCl$_3$/Et$_2$O to yield of 2-nitro-4-chloro-2'-methoxycarbonyl-diphenylsulfide 10.9 g, (93%).

To a solution of 2-nitro-4-chloro-2'-methoxycarbonyl-diphenylsulfide (10.3 g, 32 mmol) in 78% ethanol (200 mL) a solution of CaCl$_2$ (2.3 g, 19 mmol) in 4 mL water was added. Zn dust (68.9 g, 1.05 mol) was added and the mixture was refluxed for 3 h. The hot mixture was filtered through a celite pad and washed with hot ethanol. The filtrate was concentrated in vacuo to obtain a solid product 2-amino-4-chloro-2'-methoxycarbonyl-diphenylsulfide; yield 10.01 g, (98%).

To a solution of 2-amino-4-chloro-2'-methoxycarbonyl-diphenylsulfide (9.4 g, 32 mmol) in ethanol, 1N KOH (67 mL, 67 mmol) was added and the mixture was refluxed for 2 h. The ethanol was removed and the solution was cooled to 0° C. The product 2-amino-4-chloro-2'-carboxyl-diphenylsulfide was precipitated by dropwise addition of conc. HCl to pH 3. The precipitate was filtered and collected and dried; yield 8.5 g, (95%).

To a solution of 2-amino-4-chloro-2'-carboxyl-diphenylsulfide (8.4 g, 30 mmol) in dry $CH_2Cl_2$, 4-dimethylaminopyridine (1.2 g, 9 mmol) and 1-(3-dimethylaminopropyl)-3-ethylcarbodiimide hydrochloride (10.1 g, 53 mmol) were added and stirred at room temperature overnight. The solution was concentrated in vacuo, then diluted with water (200 mL) and ether (50 mL) and placed in refrigerator to precipitate out the final product 8-chloro-10,11-dihydrodibenzo[b,f][1,4]thiazepine-11-one. The precipitate was filtered and dried under vacuum; yield 7.2 g, (92%).

To a stirred solution of 8-chloro-11-oxo-dibenzo[b,f][1,4]thiazepine (0.639 g, 2.44 mmol) in dry toluene(20 mL) was added $PCl_5$ (0.610 g, 2.93 mmol) in one portion and then refluxed for 4 h. The solvent was removed in vacuo and the imino chloride was dried under vacuum. To a solution of the imino chloride (0.684 g, 2.44 mmol) in dry acetonitrile (20 mL) was added 1,8-diazabicyclo[5.4.0]-undec-7-ene (DBU) (2.0 mL, 13.4 mmol) and 1-piperonylpiperazine (1.0 g, 4.54 mmol). The mixture was refluxed overnight, cooled to room temperature and the solvent removed in vacuo. The resulting oil was diluted with ether (250 mL). The organic phase was washed with water (3×20 mL), brine (20 mL) and concentrated in vacuo. Purification of the product was conducted on silica gel using ethyl acetate:hexane (50:50) as the eluant to give 0.302 g (60%) of the product as colourless solid; m.p. 170–172° C.

The hydrochloride salt was subsequently prepared in the manner described in example 1, and the title compound was obtained as an off-white solid; m.p. 190–92° C.

EXAMPLE 8

4-chloro-11-(4-piperonyl-1-piperazinyl)-5H-dibenzo[b,e][1,4]diazepine

To a stirred solution of anisole (0.40 mL, 3.68 mmol) in dry toluene (2.00 mL) was added titanium tetrachloride (0.24 mL, 2.18 mmol) at room temperature under argon. The mixture was then treated with 1-piperonylpiperazine (2.07 g, 9.40 mmol) and 4-chloro-11-oxo-10,11-dihydro-5H-dibenzo[b,e][1,4]diazepine (0.49 g, 2.00 mmol) (Giani et al, supra) and diluted with toluene (1.00 mL). After more 1-piperonylpiperazine (1.19 g, 5.40 mmol) was added, toluene (8.00 mL) was added and the resulted reaction mixture was heated at reflux for 6 h before it was cooled to 60° C. Isopropanol (0.80 mL), celite (0.40 g) and ammonia (30%, 0.50 mL) were added sequentially and the whole mixture was filtered hot. Upon cooling to room temperature, the filtrate was concentrated in vacuo to dryness and the residue was subjected to column chromatography using ethyl acetate/hexanes (1/2) as the eluent. Thus 0.63 g (70%) of the title compound was afforded as a light yellow solid; m.p. 160–162° C.; MS 447 ($M^+$+1).

In a like manner, there was prepared the following additional compounds:

a) 7,8-dichloro-11-(4-piperonyl-1-piperazinyl)-5H-dibenzo[b,e][1,4]diazepine, 62%, m.p. 92–94° C.; MS 480 ($M^+$–1) from 7,8-dichloro-11-oxo-10,11-dihydro-5H-dibenzo[b,e][1,4]diazepine.

The sulfuric acid salt of the title compound was subsequently prepared by the following procedures: to the solution of base (30 mg, 0.062 mmol) in 0.5 mL of methanol was added sulfuric acid (0.13 mL, 1.0 M, 0.12 mmol) at room temperature. The mixture was stirred for 5 minutes, followed by the addition of diethyl ether (2.0 mL). The generated precipitate was filtered and dried under vacuum to yield 38 mg (90%) of the expected sulfuric acid salt as a light yellow solid; m.p. >270° C. (dec.); MS 579 ($M^+$), 481 ($M^+$—$H_2SO_4$).

b) 2-trifluoromethyl-11-(4-piperonyl-1-piperazinyl)-5H-dibenzo[b,e][1,4]diazepine, 92%, m.p. 76–78° C.; MS 481 ($M^+$+1) from 2-trifluoromethyl-11-oxo-10,11-dihydro-5H-dibenzo[b,e][1,4]diazepine.

c) 2,7,8-trichloro-11-(4-piperonyl-1-piperazinyl)-5H-dibenzo[b,e][1,4]diazepine, 86%, m.p. 182–185° C.; MS 515 ($M^+$+1) from 2,7,8-trichlicro-11-oxo-10,11-dihydro-5H-dibenzo[b,e][1,4]diazepine.

d) 3-chloro-11-(4-piperonyl-1-piperazinyl)-5H-dibenzo[b,e][1,4]diazepine 98%, m.p. 70–72° C.; MS447 ($M^+$+1) from 3-chloro-11-oxo-10,11-dihydro-5H-dibenzo[b,e][1,4]diazepine.

e) 2-methoxy-11-(4-piperonyl-1-piperazinyl)-5H-dibenzo[b,e][1,4]diazepine, 14%, m.p. 126–128° C.; MS 443 ($M^+$+1) from 2-methoxy-11-oxo-10,11-dihydro-5H-dibenzo[b,e][1,4]diazepine.

f) 4-nitro-11-(4-piperonyl-1-piperazinyl)dibenz[b,f][1,4]oxazepine, 55%, m.p. 142–144° C.; MS 459 ($M^+$+1) from 4-nitro-dibenz[b,f][1,4]oxazepin-11(10H)-one (Klunder et al, supra).

g) 4-cyano-11-(4-piperonyl-1-piperazinyl)dibenz[b,f][1,4]oxazepine, from 4-cyano-dibenz[b,f][1,4]oxazepin-11(10H)-one.

h) 4-chloro-11-(4-piperonyl-1-piperazinyl)dibenz[b,f][1,4]oxazepine, m.p. 146–148° C.; from 4-chlorodibenz[b,f][1,4]oxazepin-11(10H)-one.

EXAMPLE 9

2-nitro-10-(4-piperonyl-1-piperazinyl)dibenzo[b,f]thiepine

To a stirred solution of 2-nitro-10-oxo-dibenzo[b,f]thiepine (0.54 g, 2.00 mmol) and 1-piperonylpiperazine (2.04 g, 9.26 mmol) in toluene (15 mL) was added titanium tetrachloride (0.24 mL, 2.2 mmol) at room temperature under argon. The resulted mixture was heated at reflux for 3.5 h and then cooled down to room temperature. The whole mixture was poured into a saturated sodium bicarbonate solution (50 mL). After separation, the aqueous phase was extracted with dichloromethane (2×50 mL). The combined organic solution was dried ($MgSO_4$), filtered and concentrated in vacuo to dryness. The residue was subjected to column chromatography using ethyl acetate/hexanes (1/2) as eluent. Thus 0.161 g (17%) of the title compound was obtained as a yellow solid; m.p. 188–190° C.; MS 474 ($M^+$+1).

EXAMPLE 10

Receptor Binding Assay

D2 and D4 receptor-binding affinities of the compounds of examples 1 to 9 were evaluated according to their ability to reduce binding of $^3$H-spiperone as compared to the reference compound clozapine. The potency of the test compound to reduce $^3$H-spiperone binding directly correlated to its binding affinity for the receptor.

D4 Receptor Preparation

HEK 298 (human embryonic kidney) cells stably transfected with human D4 receptor (D4.2 sub-type) were grown in NUNC cell factories for 5 days (75% confluency) without a media change and removed with versene (approximately 19 mg of cells per cell factory tray). The cells were then centrifuged in a Sorval centrifuge for 10 minutes, 5000 rpm (GS3 rotor) and the pellets quickly frozen in liquid nitrogen and stored at –80° C. until used in binding assay. When used in the assay, cells were thawed on ice for 20 minutes and then 10 mL of incubation buffer (50 mM Tris, 1 mM EDTA, 4 mM $MgCl_2$, 5 mM KCl, 1.5 mM $CaCl_2$, 120 mM NaCl, pH7.4) was added. The cells were then vortexed to resuspend pellet and homogenized with a Kinematica CH-6010 Kriens-LU homogenizer for 15 seconds at setting 7. Concentration of receptor protein was determined using the Pierce BCA assaay.

D2 Receptor Preparation $GH_4C_1$ (rat pituitary) cells stably transfected with the human D2 receptor (short isoform) were grown in $CO_2$ independent media in roller bottles (1500 $cm^2$) for 10 days. 100 $\mu$M $ZnSO_4$ was added to the cells (the D2 promoter being zinc inducible). After 16 hours, fresh media was added to allow the cells to recover for 24 hours. The cells were harvested using versene and then centrifuged in a Sorval centrifuge for 10 minutes, at 5000 rpm (GS3 rotor). Pellets were quickly frozen in liquid nitrogen and stored at –80° C. until used in the binding assays. When used in the assay, cells were thawed on ice for 20 minutes. Each roller bottle produced approximately 72 mg of protein. 10 mL of incubation buffer was added to the pellets which were then vortexed, resuspended and homogenized with a Kinematica CH-6010 Kriens-LU homogenizer for 15 seconds at setting 7. The receptor protein concentration was determined using the Pierce BCA assay.

Total Spiperone Binding Assay

The incubation was started by the addition of 500 $\mu$l (50 $\mu$g protein) membrane homogenate to a solution of 900 $\mu$l incubation buffer and 100 $\mu$l (0.25 nM final conc.) $^3$H-spiperone (90 Ci/mmol Amersham diluted in borosilicalte glass vial) in 12×75 mm polypropylene tubes. The tubes were vortexed and incubated at room temperature for 90 minutes. The binding reaction was stopped by filtering using a Brandell Cell Harvester. The samples were filtered under vacuum over glass fibre filters (Whatman GF/B) presoaked for 2 hours in 0.3% polyethylenimine (PEl) in 50 mM Tris buffer (pH7.4). The filters were then washed 3 times with 5 mL ice cold 50 mM Tris buffer (pH7.4). Individual filter disks were put in scintillation vials (Biovials, Bechman). Ready Protein Plus liquid scintillant (5 mL, Beckman) was added and the vials counted by liquid scintillation spectrophotometry (Beckman LSC 6500) after equilibrating for three hours at room temperature to determine total binding (BT).

Non-Specific Binding Assay for D4

The incubation was started by the addition of 500 $\mu$l (50 $\mu$g protein) membrane homogenate to a solution of 400 $\mu$l incubation buffer, 100 $\mu$l $^3$H-spiperone (90 Ci/mmol Amersham diluted in borosilicate glass vial to 0.25 nM final conc.) and 500 $\mu$l (30 $\mu$M final conc.) of fresh dopamine (Research Biochemicals Inc., light protected and dissolved in incubation buffer) in 12×75 mm polypropylene tubes. The tubes were vortexed and incubated at room temperature for 90 minutes at which time the binding reaction was stopped by filtering. The filters were washed and counted using the same procedure as in the total binding assay described above to give the non-specific binding value (NSB).

Non-Specific Binding Assay for D2

This assay employed the same procedures as the non-specific binding assay for D4 with the exception that 2 $\mu$M (final conc.) of (–) sulpiride (Research Chemicals Inc.) was used in place of dopamine.

Displacement Binding Assay

The incubation was started by the addition to 12×75 mm polypropylene tubes 500 $\mu$l (50 $\mu$g protein) membrane homogenate to a solution of 400 $\mu$l incubation buffer, 100 $\mu$l (0.25 final conc.) $^3$H-spiperone (90 Ci/mmol, Amersham, diluted in borosilicate glass vial to) and 500 $\mu$l of test compound that was prepared from 1 mM stock dissolved in DMSO and stored at –20° C. in polypropylene cryogenic storage vials until dilution in incubation buffer in borosilicate glass vials. The tubes were vortexed and incubated at room temperature for 90 minutes at which time the binding reaction was stopped by filtering. The filters were washed and counted using the same procedure as in the total binding assay described above to give the displacement binding value ($B_D$).

Calculations

The test compounds were initially assayed at 1 and 0.1 $\mu$M and then at a range of concentrations chosen such that the middle dose would cause about 50% inhibition of $^3$H-spiperone binding. Specific binding in the absence of test compound ($B_O$) was the difference of total binding ($B_T$) minus non-specific binding (NSB) and similarly specific binding (in the presence of test compound) (B) was the difference of displacement binding ($B_D$) minus non-specific binding (NSB). $IC_{50}$ was determined from an inhibition response curve, logit-log plot of % $B/B_O$ vs concentration of test compound.

Ki was calculated by the Cheng and Prustoff transformation:

$$Ki=IC_{50}/(1+[L]/K_D)$$

where [L] is the concentration of $^3$H-spiperone used in the assay and $K_D$ is the dissociation constant of $^3$H-spiperone determined independently under the same binding conditions. Assay results are reported in the following Table:

| COMPOUND | D4 AFFINITY AND SELECTIVITY STRUCTURE | Ki | D2/D4 |
|---|---|---|---|
| clozapine | | 23 | 10 |
| 11-(4-piperonyl)-1-piperazinyl)-dibenz[b,f][1,4]oxazepine | | 30 | 32.7 |
| 8-chloro-11-(4-piperonyl)-1-piperazinyl)dibenz[b,f][1,4]oxazepine | | 4 | 23.8 |
| 8-methyl-11-(4-piperonyl)-1-piperazinyl)dibenz[b,f][1,4]oxazepine | | 143 | 9.8 |

-continued

D4 AFFINITY AND SELECTIVITY

| COMPOUND | STRUCTURE | Ki | D2/D4 |
|---|---|---|---|
| 7,8-dimethyl-11-(4-piperonyl)-1-piperzainyl)-5H-dibenzo[b,f][1,4] diazepine | 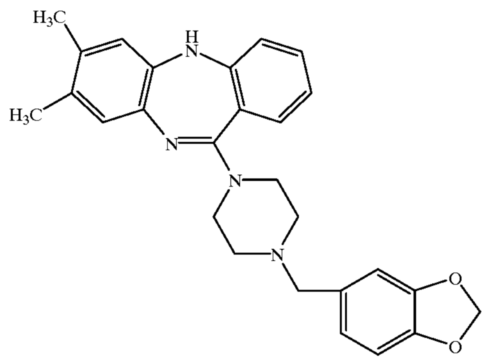 | 266 | 14.1 |
| 11-(4-piperonyl)-1-piperazinyl-5H-dibenzo[b,e][1,4]diazepine | 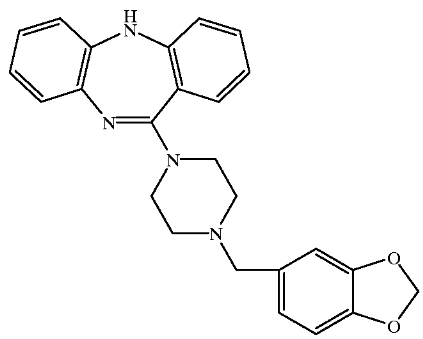 | 63 | 6 |
| 2-Chloro-11-(4-piperonyl)-1-piperazinyl-5H-dibenzo[b,e][1,4] diazepine | 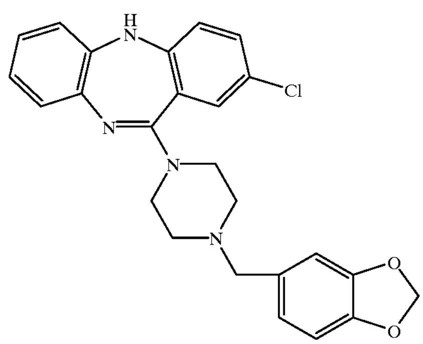 | 76 | 7.3 |
| 8-chloro-11-(4-piperonyl)-1-piperazinyl)dibenzo[b,f][1,4] thiazepine | 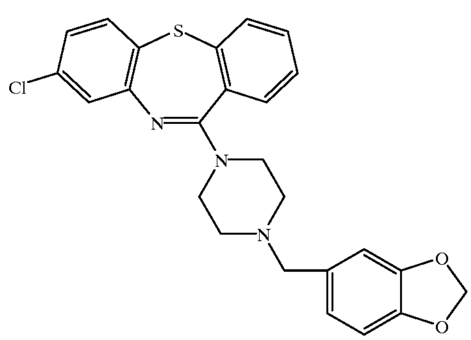 | 24 | 63 |

-continued

D4 AFFINITY AND SELECTIVITY

| COMPOUND | STRUCTURE | Ki | D2/D4 |
|---|---|---|---|
| 4-chloro-11-(4-piperonyl-1-piperazinyl)-5H-dibenzo[b,e][1,4] diazepine | 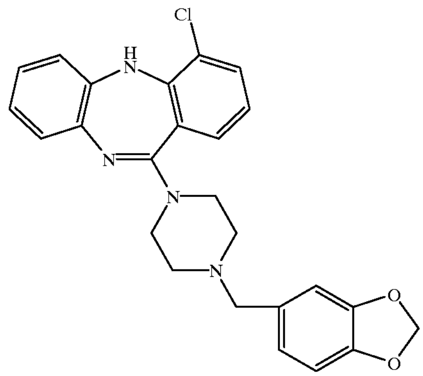 | 34 | 10.6 |
| 7,8-dichloro-11-(4-piperonyl-1-piperazinyl)-5H-dibenzo[b,e][1,4]diazepine | 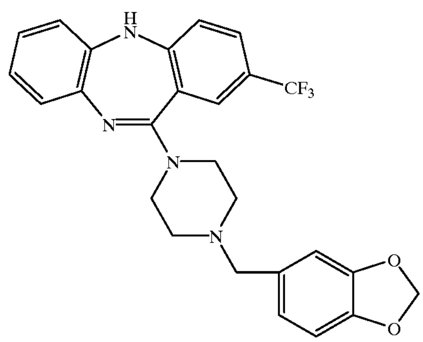 | 61 | 27.4 |
| 2-trifluoromethyl-11-(4-piperonyl-1-piperazinyl)-5H-dibenzo [b,e][1,4]diazepine | 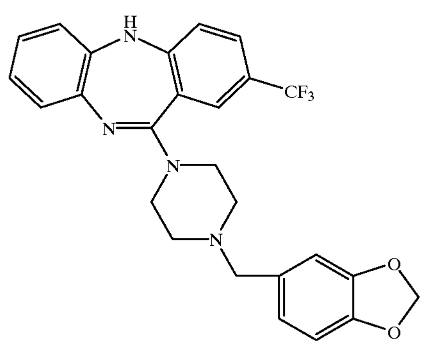 | 73.5 | 1.9 |
| 2,7,8-trichloro-11-(4-piperonyl-1-piperazinyl)-5H-dibenzo[b,e][1,4]diazepine | 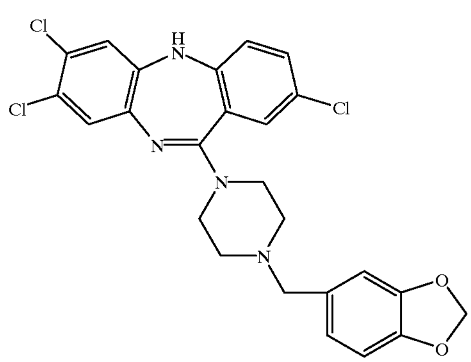 | 149 | 15.7 |

-continued
| COMPOUND | STRUCTURE | Ki | D2/D4 |
|---|---|---|---|
| 3-chloro-11-(4-piperonyl-1-piperazinyl)-5H-dibenzo[b,e][1,4]diazepine | 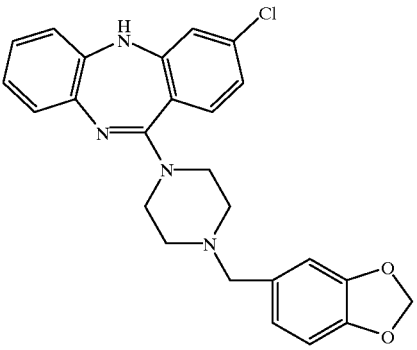 | 23.5 | 24.9 |
| 2-methoxy-11-(4-piperonyl-1-piperazinyl)-5H-dibenzo[b,e][1,4] diazepine | 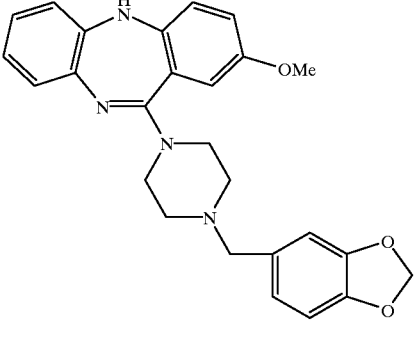 | 15 | 5.1 |
| 4-nitro-11-(4-piperonyl-1-piperazinyl)dibenz[b,f][1,4]oxazepine | 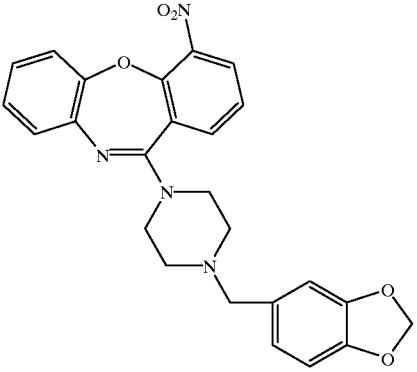 | 24.5 | 53.2 |
| 2-nitro-10-(4-piperonyl-1-piperazinyl)dibenzo[b,f]thiepine | 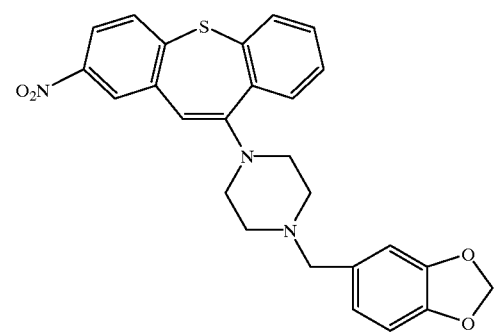 | 15.3 | 281 |
D4 AFFINITY AND SELECTIVITY

-continued
D4 AFFINITY AND SELECTIVITY

| COMPOUND | STRUCTURE | Ki | D2/D4 |
|---|---|---|---|
| 2-chloro-10-(4-piperonyl-1-piperazinyl)dibenzo[b,f]thiepine | 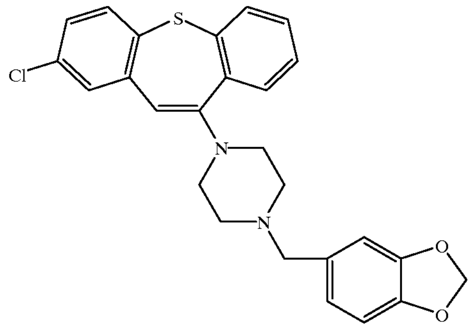 | 8.3 | 15.9 |
| 4-cyano-11-(4-piperonyl-1-piperazinyl)dibenz[b,f][1,4]oxazepine | 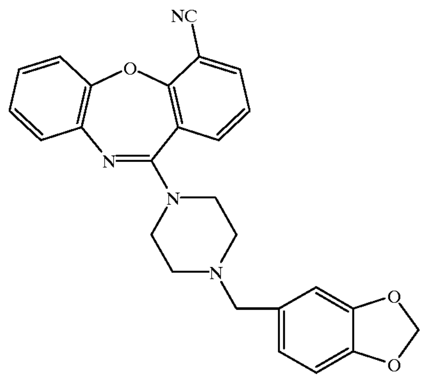 | 119 | 82.1 |
| 4-chloro-11-(4-piperonyl-1-piperazinyl)dibenz[b,f][1,4]oxazepine | 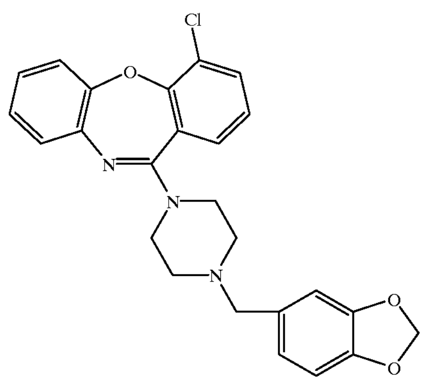 | 57 | 99.2 |

EXAMPLE 11

Functional Assay

The D4 receptor responds to dopamine and other agonists by reducing adenyl cyclase mediated production of cyclic AMP. Particular test compounds were assayed for their ability to reverse dopamine inhibition of adenyl cyclase by the following procedure. Forskolin was used to elevate the basal adenyl cyclase activity.

CHO Pro 5 cells stably expressing human D4 receptors were plated in 6 well plates in DMEM (Dulbecco's Modified Eagle Medium)/F12(Nutrient Mixture F12 (Ham)) media with 10% FCS (fetal calf serum) and G418 (Geneticen Disulfate), and incubated at 37° C. in a $CO_2$ incubator. The cells were allowed to grow to about 70% confluence before use in the assay.

Antagonist Assay

The culture media of each well was removed by aspiration, and the wells were washed once with serum free media (SFM) (DMEM/F12) media. Then 2 mL of fresh SFM+IBMX media (SFM with 0.5 mM IBMX (3-isobutyl-1-methylxanthine 0.1% ascorbic acid and 10 μM pargyline) was added to each well and then incubated at 37° C. for 10 minutes in $CO_2$ incubator. Following incubation, SFM+IBMX media was aspirated and fresh SFM+IBMX media was added to wells separately with one of a) forskolin (10 μM final conc.); b) dopamine and forskolin ( both 10 μM final conc.); and c) test compound (1 and 0.1 μM), and dopamine and forskolin (both 10 μM final conc.). Basal adenyl cyclase activity was determined from wells with only SFM+IBMX media added.

The cells were then incubated at 37° C. for 30 minutes in a $CO_2$ incubator. Following incubation the media was aspirated from each well and then washed once with 2 mL of PBS (phosphate buffered saline). Each well was then treated with 1 mL cold 95% ethanol: 5 mM EDTA (2:1) at 4° C. for 1 h. The cells from each well were then scraped and transferred into individual Eppendorf tubes. The tubes were centrifuged for 5 minutes at 4° C., and the supernatants were transferred to new Eppendorf tubes. The pellets were discarded and the supernatants dried using a SpeedVac. The extracts were then reconstituted in 600 μL of 0.1 M sodium acetate buffer, pH 6.1, and stored at 4° C. until assayed for cAMP concentration. cAMP content measured in fmoles/well for each extract was determined by EIA (enzyme-immunoassay) using Amersham Biotrak cAMP EIA kit (Amersham RPN 225).

Total inhibition ($I_O$) of forskolin-stimulated adenyl cyclase activity by dopamine was determined as the difference in concentration of cAMP in the forskolin-treated cells ($C_f$) and dopamine-forskolin treated cells ($C_d$).

$$I_O = C_f - C_d$$

Net inhibition (I) of forskolin-stimulated adenyl cyclase activity by dopamine in the presence of an antagonist was determined as the difference in concentration of cAMP in the forskolin-treated cells ($C_f$) and test compound, dopamine and forskolin treated cells (C).

$$I = C_f - C$$

The ability of a test compound to reverse the dopamine inhibition (% reversal, % R) was determined by the formula:

$$\% R = (1 - I/I_O) \times 100$$

| Antagonist Activity | | |
|---|---|---|
| | % REVERSAL OF DOPAMINE EFFECT | |
| COMPOUND | 1 μM | 10 μM |
| clozapine | 10 | 62 |
| 11-(4-piperonyl)-1-piperazinyl)-dibenz[b,f][1,4]oxazepine | 40 | 50 |
| 8-chloro-11-(4-piperonyl)-1-piperazinyl)-dibenz[b,f][1,4]oxazepine | 46 | 68 |
| 3-chloro-11-(4-piperonyl-1-piperazinyl)-5H-dibenzo[b,e][1,4]diazepine | 19 | 50 |
| 2-chloro-10-(4-piperonyl-1-piperazinyl)dibenzo[b,f]thiepine | 47 | 40 |

Agonist Assay

To D4 stably expressing CHO cells prepared as previously described were added test compound and forskolin (10 μM final concentration). The cells were incubated, extracted and measured for cAMP concentration as above. Agonist activity of a test compound would result in a decrease in cAMP concentration compared to cells treated with forskolin ($C_f$) only. No decrease was observed for any of the compounds tested, therefore none exhibited dopamine agonist activity. It is predicted based on structural and biological functional similarities that the remaining compounds of the invention would also exhibit dopamine antagonist activity.

We claim:

1. A compound of Formula I:

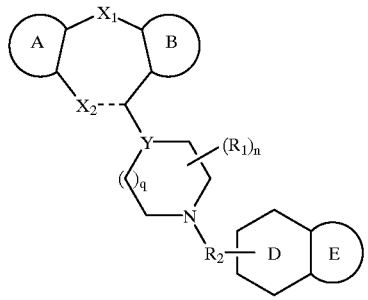

wherein:

A and B independently are both benzene optionally substituted with 1 or 2 substituents selected independently from hydroxyl, halo, selected independently from hydroxyl, halo, $C_{1-4}$alkyl, amino, nitro, cyano, halo-substituted $C_{1-4}$alkyl, $C_{1-4}$alkoxy, halo-substituted $C_{1-4}$alkoxy, $C_{1-4}$alkoxycarbonyl, $C_{1-4}$acyl, halo-substituted $C_{1-4}$acyl cyclo-$C_{1-7}$alkyl, thio-$C_{1-4}$alkylene, $C_{1-4}$alkylthio, halo-substituted $C_{1-4}$alkylthio, cyanothio, tetrazolyl, N-piperidinyl, N-piperazinyl, N-morpholinyl, acetamido, $C_{1-4}$alkylsulfonyl, halosulfonyl, halo-substituted $C_{1-4}$alkylsulfonyl, $C_{1-4}$alkylsulfoxyl, sulfonamido $C_{1-4}$alkylseleno, and $OSO_3H$;

$X_1$ is selected from NH, N—$C_{1-4}$alkyl and N-acetyl, $X_2$ is N=

Y is selected from CH and N;

$R_1$ represents $C_{1-4}$alkyl;

n is 0, 1 or 2;

q is 1 or 2;

$R_2$ is $C_{1-6}$alkylene optionally incorporating an intervening or terminating heteroatom selected from N, O and S;

D is cyclohexane or benzene; and

E is a saturated or unsaturated 5- or 6-membered heterocycle incorporating 1, 2 or 3 heteroatoms selected from O, N, and S, wherein E is optionally substituted with 1 or 2 substituents selected from halogen, $C_{1-4}$alkyl and halogen-substituted $C_{1-4}$alkyl;

and acid addition salts, solvates or hydrates thereof.

2. A compound according to claim 1, wherein $X_1$ is NH.

3. A compound according to claim 1, wherein $X_1$ and $X_2$ - - - with rings A and B form a tricycle selected from 5H-dibenzo[b,e][1,4]diazepine that is substituted by one of 7,8-dichloro, 7,8-dimethyl, 2-chloro, 3-chloro, 4-chloro, 2,4-chloro, 4,7,8-trichloro, 2-trifluoromethyl 1-fluoro, or 2-methoxy; dibenz[b,f][1,4]oxazepine that is substituted by one of 4-nitro, 8-chloro, 4-cyano or 4-chloro; dibenzo[b,f]thiepine that is substituted by one of 2-nitro or 2-chloro; 11H-dibenzo[b,f]thiepin that is substituted by 2-methylthio; and dibenzo[b,f][1,4]thiazepine that is substituted by 8-chloro.

4. A compound according to claim 3, wherein ring D is benzene.

5. A compound according to claim 3, wherein $R_2$ is —$CH_2$—.

6. A compound according to claim 3, wherein ring E is a 5-membered heterocycle containing two heteroatoms.

7. A compound according to claim 6, wherein ring E contains two oxygen atoms.

8. A compound according to claim 3, wherein ring E is a six-membered heterocycle containing two heteroatoms.

9. A compound according to claim 8, wherein ring E contains two oxygen atoms.

10. A compound according to claim 6, wherein ring D is benzene.

11. A compound according to claim 10, wherein $R_2$ is —$CH_2$—.

12. A compound according to claim 3, wherein $R_2$ together with rings D and E form a piperonyl group.

13. A pharmaceutical composition, comprising a therapeutically effective amount of a compound according to claim 1, and a pharmaceutically acceptable carrier.

14. A compound according to claim 1, wherein substituents for A and B are selected independently from hydroxyl, halo, $C_{1-4}$alkyl, amino, nitro, cyano, halo-substituted $C_{1-4}$alkyl, $C_{1-4}$alkoxy, halo-substituted $C_{1-4}$alkoxy, $C_{1-4}$alkoxycarbonyl, $C_{1-4}$acyl, halo-substituted $C_{1-4}$acyl, cyclo-$C_{1-7}$alkyl, thio-$C_{1-4}$alkylene, $C_{1-4}$alkylthio, halo-substituted $C_{1-4}$alkylthio, cyanothio, tetrazolyl, N-piperidinyl, N-piperazinyl, N-morpholinyl, acetamido, $C_{1-4}$alkylsulfonyl, halosulfonyl, halo-substituted $C_{1-4}$alkylsulfonyl, $C_{1-4}$alkylsulfoxyl, sulfonamido, $C_{1-4}$alkylseleno, and $OSO_3H$.

15. A pharmaceutical composition for treating a condition mediated by the D4 receptor, comprising a compound according to claim 1 in an amount effective to inhibit the D4 receptor, and a pharmaceutically acceptable carrier therefor.

16. A method for the treatment of anxiety or schizophrenia, comprising the step of administering to a mammal in need of such treatment a composition according to claim 15.

17. A pharmaceutical composition for treating schizophrenia, comprising a compound according to claim 1 in an amount sufficient to produce an antischizophrenia effect, and a pharmaceutically acceptable carrier therefor.

18. A method for the treatment of schizophrenia, comprising the step of administering to a mammal in need of such treatment, a composition according to claim 17.

19. A pharmaceutical composition for treating anxiety, comprising a compound according to claim 1, an amount sufficient to produce an anti-anxiety effect, and a pharmaceutically acceptable carrier therefor.

20. A method for the treatment of anxiety, comprising the step of administering to a mammal in need of such treatment, a composition according to claim 19.

* * * * *